(12) United States Patent
Abe (10) Patent No.: US 8,148,058 B2
(45) Date of Patent: Apr. 3, 2012

(54) METHOD FOR SCREENING ALLERGIC DISEASE-RELATED MOLECULE AND CELL LINES TO BE USED IN THE METHOD

(75) Inventor: Ryo Abe, Nagareyama (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 303 days.

(21) Appl. No.: 12/514,799

(22) PCT Filed: Nov. 14, 2007

(86) PCT No.: PCT/JP2007/072132
§ 371 (c)(1),
(2), (4) Date: Jun. 30, 2009

(87) PCT Pub. No.: WO2008/059900
PCT Pub. Date: May 22, 2008

(65) Prior Publication Data
US 2010/0184114 A1 Jul. 22, 2010

(30) Foreign Application Priority Data

Nov. 14, 2006 (JP) .................................. 2006-308221
Mar. 5, 2007 (JP) .................................. 2007-054244

(51) Int. Cl.
*C12Q 1/00* (2006.01)
*G06K 9/00* (2006.01)
(52) U.S. Cl. ............. 435/4; 382/128; 382/133; 382/134
(58) Field of Classification Search ........................ None
See application file for complete search history.

(56) References Cited

U.S. PATENT DOCUMENTS 4,559,310 A 12/1985 Cantor
7,192,752 B2 * 3/2007 Xu et al. .................... 435/173.1

FOREIGN PATENT DOCUMENTS

| JP | 63-164883 | 7/1988 |
| JP | 2004-215581 | 8/2004 |
| JP | 2007-129941 | 5/2007 |

OTHER PUBLICATIONS

Seder et al. PNAS 1991;88:2835-9.*
Sakai et al. J Nutr Sci Vitaminol 2006;52:327-32.*
Shin-ichi Konno et al, "Suppressive effects of IPD-1151T(suplatast-tosilate) on induction of mast cells from normal mouse splenocytes", European Journal of Pharmacology vol. 259(1994), pp. 15-20.
Chyin-Song Hsieh et al, "Differential regulation of T helper phenotype development by interleukins 4 and 10 in an $\alpha\beta$ T-cell-receptor transgenic system", Proc. Natl. Acad. Sci. USA, vol. 89, pp. 6065-6069, Jul. 1992.
Hu Zhi-Qing et al. "Effect of lipopolysaccharide on mouse mast cell induction by a splenic cell culture system" Infection and Immunity, vol. 62, No. 9, 1994, pp. 3844-3849.
Corresponding EPO Official communication, EPO search report Jan. 27, 2010.

* cited by examiner

*Primary Examiner* — Q. Janice Li
(74) *Attorney, Agent, or Firm* — Solaris Intellectual Property Group, PLLC

(57) ABSTRACT

An allergic disease-related substance is screened from candidate substances based on the reactivity to a plurality of cell lines, which are basophil-like or mast cell-like cell lines derived from the same spleen tissue and have different sensitivities to allergic cytokines. Further, an allergic disease-related substance is screened from candidate substances using at least one basophil-like or mast cell-like cell lines selected from the group consisting of R cell (Deposit No. FERM BP-10918), N 62.5 cell (Deposit No. FERM BP-10919) and RCCM cell (Deposit No. FERM BP-10920).

11 Claims, 5 Drawing Sheets

METHOD FOR SCREENING ALLERGIC DISEASE-RELATED MOLECULE AND CELL LINES TO BE USED IN THE METHOD

TECHNICAL FIELD

The present invention relates to a method for screening an allergic disease-related molecule and cell lines to be used in the method.

BACKGROUND ART

In so called allergic diseases which develop atopic dermatitis, bronchial asthma, food allergy, and the like, an allergen enters the body and combines with IgE on mast cells or basophils. Then, local inflammation is induced by histamine secreted from these cells. In order to produce IgE, functional differentiation of T cells that produce Th2 cytokines such as IL-4 or IL-13 that are important for class switching of immunoglobulin is important, and thus allergic constitution is considered to be in a state of Th2 dominance. Th2 cytokines such as IL-3, IL-4, IL-6, or IL-13 play a critical role in the proliferation or differentiation of effector cells such as mast cells or basophils.

Thus, the cytokines are involved in various reactions. Therefore, when sensitivities of these cells to these cytokines vary, big differences in the resultant reactivity may be caused. It is considered that the sensitivity of effector cells to cytokines is increased in an area where the allergic-inflammation occurred.

On the other hand, there have been many attempts to elucidate allergy-related phenomena at the molecular level using a specific cell line. As such a cell line, a novel mast cell line which maintains the functions of mast cells and does not involve c-Kit autophosphorylation is known (Japanese Patent Application Laid-Open (JP-A) No. 2004-215581). Therefore, it is suggested that the cell line, an NCL-2 cell line, is likely to exhibit a similar response to drug stimulation to that of a normal mast cell line because the cell line is not a tumor mast cell line. Consequently, it is described that the proliferation, differentiation, and functions of mast cells can be analyzed in detail by using this cell line.

DISCLOSURE OF THE INVENTION

However, because the above-described cell line was found as an independent cell line similar to a normal mast cell, the intensity of the sensitivity of the cell line to cytokines is not clear. Therefore, the cell line is unsuitable for efficiently screening for a substance involved in a chronic allergic condition in some cases.

Therefore, an objective of the present invention is to provide a screening method that can efficiently screen an allergic disease-related substance, and cell lines to be used in the method.

According to the invention, there is provided a method of screening an allergic disease-related molecule, the method including screening for an allergic disease-related substance from a candidate substance based on reactivity to a plurality of cell lines which are basophil-like or mast cell-like cell lines derived from the same spleen tissue and have different sensitivities to allergic cytokines.

It is preferable that the cell lines are at least two selected from the group consisting of an R cell (Accession No. FERM BP-10918), an N62.5 cell (Accession No. FERM BP-10919), and an RCCM cell (Accession No. FERM BP-10920).

In a second screening method of the invention, if the properties of the above-described R cell, N62.5 cell, and RCCM cell are utilized, one or more of these cell lines may be used. That is, the second screening method of the invention is a method of screening an allergic disease-related molecule, the method including screening for the allergic disease-related substance from candidate substances using at least one basophil-like or mast cell-like cell line selected from the group consisting of an R cell (Accession No. FERM BP-10918), an N62.5 cell (Accession No. FERM BP-10919), and an RCCM cell (Accession No. FERM BP-10920).

Further, the screening method of the invention may include steps of contacting the cell line with the candidate substance and screening the candidate substance based on the reaction of the cell line after the contacting. The step of screening may include screening candidate substances with different reactivities to a plurality of cell lines used for screening.

Further, the screening method of the invention may be performed in the presence of a competitive compound.

A cell set of the invention is a set that includes at least two selected from the group consisting of an R cell (Accession No. FERM BP-10918), an N62.5 cell (Accession No. FERM BP-10919), and an RCCM cell (Accession No. FERM BP-10920) and is used for screening an allergic disease-related compound.

According to the invention, the plurality of cell lines which are basophil-like or mast cell-like cell lines derived from the same spleen tissue and have different sensitivities to allergic cytokines are used to screen for an allergic disease-related substance from candidate substances. Since the plurality of cell lines are originally derived from the same tissue, it is thought that differences in genetic characteristics between the cell lines are smaller than those between the cell lines and a cell line derived from other tissues and, further, that differences in sensitivities to cytokines are caused by these smaller differences in genetic characteristics. For this reason, candidate substances which exhibit different reactivities to the plurality of cell lines are recognizing differences in cell lines corresponding to differences in sensitivities to allergic cytokines. As a result, candidate substances which are likely to be pertinent to the sensitivity of allergic cytokines can be efficiently screened by using such cell lines.

According to the invention, there can be provided a screening method that can efficiently screen an allergic disease-related substance and cell lines to be used in the method.

BRIEF DESCRIPTION OF THE DRAWINGS

[FIG. 1] (A) is a graph showing the proliferative response of an R cell, an N62.5 cell, and an RCCM cell to 10% by volume of RCGF containing a culture medium, according to the Examples of the present invention; (B) is a graph showing the proliferative response of an R cell, an N62.5 cell, and an RCCM cell to 0.1% by volume of RCGF containing a culture medium, according to the Examples of the present invention; (C) is a graph showing the proliferative response of an R cell, an N62.5 cell, and an RCCM cell to 0% by volume of RCGF containing a culture medium, according to the Examples of the present invention.

BEST MODE FOR CARRYING OUT THE INVENTION

The screening method of the present invention is the screening method of an allergic disease-related molecule including screening for an allergic disease-related substance from candidate substances based on the reactivity to a plurality of cell lines which are basophil-like or mast cell-like cell lines derived from the same spleen tissue and have different sensitivities to allergic cytokines.

Since the present cell lines are basophil-like or mast cell-like cell lines, they have sensitivity to an allergic disease-related substance. Here, "basophil-like or mast cell-like" refers to characteristics that can be determined by morphology observation by light or electron microscopes or cell surface antigens. For example, a basophil-like morphology can be characterized by a cyst-like structure with a low granule density and the morphology that is not stained by Toluidine-blue (TB) staining. On the other hand, a mast cell-like morphology can be characterized by the characteristics of a cell surface molecule, where c-kit and FcεRIα are double-positive.

Specific examples of the such cell line include a basophil-like or mast cell-like cell line that appears while spleen cells are cultured with an ovalbumin (OVA antigen) peptide for a long period of time and a basophil-like or mast cell-like cell line induced from the spleen cells of a DO11.10 T cell receptor (TCR) transgenic mouse using an OVA antigen. The 323rd to 339th amino acid residues of an OVA antigen peptide may be used to produce the basophil-like or mast cell-like cell lines.

Examples of the cell lines in the invention include an R cell (National Institute of Advanced Industrial Science and Technology, International Patent Organism Depositary; Tsukuba Central 6, 1-1-1 Higashi, Tsukuba, Ibaraki, Deposited on 1 Sep., 2005; Accession No. FERM BP-10918), an N62.5 cell (National Institute of Advanced Industrial Science and Technology, International Patent Organism Depositary; Deposited on 16 Nov., 2006; Accession No. FERM BP-10919), and an RCCM cell (National Institute of Advanced Industrial Science and Technology, International Patent Organism Depositary; Deposited on 16 Nov., 2006; Accession No. FERM BP-10920).

These cells can be obtained by removing T cells from spleen cells that have been long-term cultured in the presence of an OVA antigen for isolation and then long-term subculturing using various concentrations of a culture supernatant of an OVA-specific T cell line (R cell growth factor: RCGF). The RCGF is a culture supernatant obtained by stimulating the OVA-specific T cell line by using an anti-T cell receptor antibody for crosslinking.

Therefore, these cell lines have the same or very similar characteristics except for the sensitivities of the cells to cytokines. Thus, it is considered that it is suitable for screening of molecules to control the proliferation of basophils or mast cells under different cytokine environments which are likely to occur in an allergic-inflamed spot.

Examples of the maintenance conditions for R cells and N62.5 cells may include coculture with OVA antigenic peptide-stimulated T cells.

T cells to be used for coculture should be helper T cells (surface marker CD4CD8−). Examples of the origin of the T cells may include mammals, and rodents in particular. Preferable examples include mice, and particularly preferable examples include mice having the same genetic strain as R cells and N62.5 cells. Any T cells may be used for coculture as long as they satisfy the above-described conditions. Particularly, it is preferable that T cells are parent cells used to establish R cells and N62.5 cells and belong to the spleen cells of DO11.10 TCR transgenic mice (hereinafter referred to as syngeneic T cells).

The concentration of OVA antigen peptide in a coculture may be 100 nM to 1000 nM and preferably 250 nM to 1000 nM.

The growth of R cells and N62.5 cells can be maintained by culturing these cells using a culture medium containing a culture supernatant of a DO11.10 T cell line or a culture medium containing IL-3 while receiving stimulation by the culture media. In order to maintain characteristic activities of these cells, it is preferable that the growth of these cells are maintained using a culture medium containing a culture supernatant of a DO11.10 cell line. Further, R cells and N62.5 cells may also be maintained and proliferated in the same manner as described above by using a culture medium containing a culture supernatant obtained by culturing a helper T cell while imparting stimulation to T cell receptors (TCR)

A culture supernatant of an OVA antigenic peptide-stimulated T cell or a culture supernatant of a TCR-stimulated T cell should be contained in the culture medium for cells. The amount may be appropriately changed depending on the state of the cells and is preferably 0.01 to 10% by volume, and particularly preferably 10% by volume for N62.5 cells, and 2.5% by volume for R cells.

When a culture medium containing IL-3 is used in place of a culture supernatant of an OVA antigenic peptide-stimulated T cell, the IL-3 contained in the culture medium may be set up depending on the state of the R cell or N62.5 cell.

Since an RCCM cell can be cultured independent of culture supernatants and growth factors, ordinary culture media for cell culture may be used.

Examples of the ordinary culture medium for various cells may include Dulbecco's modified Eagle's medium (DMEM), RPMI1640 or the like. Various additives applicable to ordinary cell cultures such as serum, various vitamins, or various antibiotics may be added as usual to these culture media.

The plurality of cell lines according to the invention are cell lines which exhibit different sensitivities to allergic cytokines.

The term "allergic cytokine" used herein includes Th2 cytokine Examples of Th2 cytokine may include IL-3, IL-4, IL-6, IL-10, IL-13 or the like. The cell lines according to the invention exhibit different reactivities depending on the type and concentration of these allergic cytokines.

The term "reactivity" used herein means the capability to change the characteristics of a cell in response to stimulation from the outside. Examples of a change in the characteristics of a cell include changes in cell morphology and cell activity such as the morphology of a cell, growth rate, survival ratio, or production of specific cellular factors; biochemical changes in molecules involved in intracellular signal transduction; and changes in genetic control such as gene expression or gene regulation. Among these changes in the state of the cells, at least one change may be used as an indicator of reactivity.

Among cell lines according to the invention, RCCM cells have a very low dependency on the above-described allergic cytokines. It is known that RCCM cells can be grown in the presence or absence of the allergic cytokines. It is observed that FcεRIα, c-kit, ClassI, or the like is present on the cell surface of an RCCM cell.

An R cell is a cell line which shows a moderate dependency on the above-described allergic cytokines. Therefore, it is confirmed that an R cell cannot survive in a culture system in the absence of allergic cytokines, but proliferates when a very slight concentration of allergic cytokines are present. An R cell has a high sensitivity to a plurality of cytokines and has growth potential, particularly against interleukins such as IL-3, IL-4, IL-5, IL-6, IL-9, IL-13, L-15 or the like, featuring Th2 type cytokine. It shows a high growth potential against IL-3, IL-4, IL-5, IL-6, IL-9, or IL-13, particularly against IL-3, IL-4, and IL-9. For example, in the case of IL-3, when the concentration is about 5 ng/ml, an R cell can be maintained, and, on the other hand, an R cell does not show sensitivity to IL-2, IL-7, IL-10, GM-CFS, or IFN-γ. It is observed that FcεRIα, c-kit, ClassI, or the like are present on the cell surface of an R cell.

An N62.5 cell is a cell line which shows a high dependency on the above-described allergic cytokines. Therefore, it is confirmed that an N62.5 cell cannot survive in the absence of the allergic cytokines, but proliferates when the concentration is higher than the concentration at which an R cell can proliferate. For example, in the case of IL-3, an N62.5 cell can be maintained when the concentration is about 20 ng/ml. It is observed that FcεRIα, c-kit, ClassI, or the like are present on the cell surface of an N62.5 cell.

Thus, it is confirmed that, although both R cells and N62.5 cells show dependency on allergic cytokines, their dependency levels are different. Comparing among the three cells, an N62.5 cell with high dependency can be used as a model system in a normal condition where it does not react when a high concentration of allergic cytokine is not present. On the other hand, an R cell with moderate dependency can be used as a so-called model system in an allergic state since it exhibits reactivity to a low concentration of allergic cytokine In contrast, an RCCM cell with a very low dependency to allergic cytokines can proliferate even when a low concentration of allergic cytokine is present and can be used as a model system for a chronic allergy.

The screening method of the invention includes screening for an allergic disease-related substance from candidate substances based on reactivity to a plurality of cell lines. As a result, the allergic disease-related substance can be efficiently screened based on differences in reactivities among the plurality of cells used for screening.

Further, the second screening method of the invention may include utilizing the characteristics of R cells, N62.5 cells, and RCCM cells according to the invention and screening for the allergic disease-related substance from candidate substances using at least one of these cells.

Specifically, it is preferable that the screening method of the invention includes the steps of contacting the cell line(s) of the invention with the candidate substance and screening the candidate substance based on the reaction of the cell line(s) after the contacting.

The candidate substance may be a substance for screening a known substance which proliferates basophil-like or mast cell-like cells, or an unidentified substance as a causative factor which proliferates basophil-like or mast cell-like cells.

Examples of the candidate substance may include natural or synthetic low molecular weight compounds and polymeric compounds. Further, various cell culture supernatants which may include known or unknown cytokines may be used as the candidate substance. In this case, the cell culture supernatant containing the substance which proliferates the basophil-like or mast cell-like cell lines can be screened. These candidate substances may be added to the culture medium at various concentrations, preferably at a plurality of concentration gradations.

In the contacting of the candidate substances with the cell lines, the candidate substances may be respectively added to the culture system to independently culture the plurality of cell lines according to the invention.

Further, the first and second screening methods may be carried out in the culture system of a cell line in the presence of a competitive compound. By using a competitive compound, a substance which inhibits the reaction induced from the contacting with the competitive compound can be screened from the candidate substances.

As with the candidate substances, examples of the competitive compound may include natural or synthetic low molecular weight compounds, polymeric compounds, cell culture supernatants, and the like. The competitive compound may be added to the culture medium at any concentration.

A competitive compound is a compound of an allergic disease-related substance in which the reactivity to the cell line to be used is known. Examples thereof may include cytokines such as IL-3, IL-4, IL-9, and the like. Additionally, the above-described RCGF may be used as the competitive compound. Since it is confirmed that these cytokines or RCGF have proliferative activity with respect to the cell lines of the invention, the substance with proliferation inhibiting activity can be screened by allowing these compounds to be present in the same system.

Ordinary culture media for proliferation may be used as the culture medium to be used for screening, and complete synthetic media, serum-free culture media, or the like may be used in order to more exactly determine characteristics of candidate substances.

As for culture conditions such as culture temperature or humidity which are applied to screening, general culture conditions for mast cells or basophil-like cell lines may be applied without any changes. Further, pre-culture may be carried out before the culture process.

The culture period varies depending on the type and state of the cell lines, but in general, it may be 2 to 7 days, preferably 3 to 5 days.

The screening of the candidate substance is carried out based on changes in the reactivity of a cell line. For example, when one cell line grows differently from other cell lines, it may be determined that the candidate substance contained in the culture system may be the allergic disease-related substance.

It is preferable that the step of screening is carried out based on the reaction of the cell line after the contacting. The reaction of such a cell line may be at least one of the indicators of the reactivity of the cell as described below. Examples may include changes in cell morphology and cell activity such as morphology of cell, growth rate, survival ratio, or production of specific cellular factors; biochemical changes in molecules involved in intracellular signal transduction; and changes in genetic control such as gene expression or gene regulation. Among changes in a cell, examples of changes in cell morphology may include changes in granule state, size and the like. Examples of changes in cell activity may include changes in production of specific factors and the like. Examples of biochemical changes may include phosphorylation, dephosphorization, and ubiquitination of molecules involved in intracellular signal transduction and the like. Further, examples of changes in genetic control may include the presence or absence of expression of specific genes, changes in the expression amount of specific genes and the like.

For example, screening can be carried out on the basis of the proliferation of cells. As a result, candidate substances which allow cells to proliferate can be screened reliably and simply. Therefore, this screening is preferable from the viewpoint of the convenience of the assay. With reference to the speed of proliferation of cell lines, various means usually used for the purpose may be applied without any changes. Examples of the means may include measurement of cell number using a hemacytometer based on visual observation or microscope and the uptake amount of radioisotope (e.g., $^3$H-thymidine) and the like.

The screening method may involve screening for candidate substances based on the gene expression involved in the proliferation of basophils or mast cell-like cells. In this case, the screening method further includes the steps of contacting cell lines of the invention with candidate substances and detecting the gene expression induced by the contacting. For example, a microarray or the like may be used to detect the induced gene expression from the viewpoint of the treatment efficiency.

Particularly, when a plurality of cell lines are used, candidate substances with different reactivities to a plurality of cell lines used for screening are screened. Since the screening for an allergic disease-related substance is carried out in the presence of candidate substances based on reactivity to a plurality of cell lines, which have different sensitivities to allergic cytokines, the allergic disease-related substance can be efficiently screened based on the difference between the response to one cell line and the response to another cell line.

For example, as the candidate substance, if there is a compound which does not affect the growth rate of either of an N62.5 cell with high dependency on allergic cytokines and an R cell with moderate dependency on allergic cytokines and, on the other hand, suppresses only a RCCM cell with a low dependency on allergic cytokines, the compound may be screened as a substance which can particularly relate to a chronic allergic disease. Further, in the same screening with the culture system in the presence of IL-3 as the competitive compound, if the compound screened as a substance which may particularly relate to a chronic allergic disease does not exhibit proliferation-inhibiting activity with respect to an RCCM cell, the compound may further be screened as a substance which may relate to an IL-3 molecule.

The combination of the cell lines may be properly selected according to the screening of the candidate substance to be targeted.

Thus, the substance to be screened based on the cytokine sensitivity may have a function to control the cytokine sensitivity. Therefore, it is preferable that the candidate substance being screened by the screening method of the invention is a candidate substance for a compound having the function to control the cytokine sensitivity.

The allergic disease which can be screened may be any disease in which an allergic cytokine is released by the activation of a T cell triggered by the entering of an allergen into the living body and the proliferation of effector cells (mast cells, basophils, etc.) in the allergic response and the release of a mediator of inflammation are considered to be caused. Examples thereof may include atopic dermatitis, bronchial asthma and the like, and, particularly, chronic (intractable) diseases.

EXAMPLES

Hereinafter, the invention will be specifically described with reference to Examples, but it is not to be construed as being limited thereto. In Examples, unless otherwise indicated, all percentages are by weight.

Example 1

Production of Cell Lines

The spleens were extirpated from ten-week-old female DO11.10 TCR transgenic mice (donated by Professor Ken Murphy, University of Washington, U.S.). The spleen cells were cultured under conditions where OVA antigen peptides (chicken OVA (cOVA) 323-339 peptide: ISQAVHAA-HAEINEAGR: SEQ ID NO 1) were added to an RPMI culture medium (10% by volume of FCS, 100 U/ml of potassium penicillin G, and 100 μg/ml of streptomycin sulfate were added: hereinafter simply referred to as a culture medium containing 10% serum) so as to give a final concentration of 1000 nM or 250 mM.

T cells showing OVA antigenic peptide reactivity were obtained from the resulting culture. The T cells were cultured while they were stimulated by anti-CD-3 antibodies at 37° C. for 24 hours and a culture supernatant (R cell growth factor-containing solution: RCGF) was obtained. Hereinafter, when the RCGF was used for cultivation, the RCGF obtained by culturing for two days was mixed with a new culture medium at a rate of 25% by volume (v/v).

Further, anti-Thy1.2 antibodies (manufactured by Pharmingen) and complement (rabbit serum, manufactured by Pel-Freeze) were respectively added to the resulting culture at 1 μg/ml and at a final concentration of 10% by volume per $1 \times 10^7$ cells/100 μl. After about 30 minutes of reaction, T cells were obtained therefrom and the cultivation was continued while the RCGF was added at various concentrations. Then cell lines according to the invention were obtained.

As a result, N62.5 cells could be maintained and proliferated in the culture medium containing 10 v/v % of RCGF and R cells could be maintained and proliferated in the culture medium containing 2.5 v/v % of RCGF. In contrast, RCCM cells could be maintained in the culture medium without RCGF.

Thereafter, respective cell lines were cultured in accordance with the dilution method over the course of three weeks and cloned. R cells were cultured in an RPMI culture medium containing 10% by volume of serum which contained 25% by volume of RCGF (or a culture medium for R cells containing 5 ng/ml of IL-3) at 37° C. in 5% $CO_2$ atmosphere and maintained. The R cells died when the RCGF and T cells were removed from the culture environment.

Example 2

Analysis of Characteristics of Cell Lines

With reference to R cells (Accession No. FERM BP-10918), N62.5 cells (Accession No. FERM BP-10919), and RCCM cells (Accession No. FERM BP-10920) which were obtained in the above-described manner, surface antigen analysis was carried out using various antibodies.

Fluorochrome (FITC) conjugated antibodies such as anti-mouse c-kit antibody (manufactured by e-Bio), anti-mouse FCε RI antibody (manufactured by e-Bio), anti-mouse B220 antibody (manufactured by e-Bio), anti-mouse CD3 antibody (manufactured by e-Bio), anti-mouse FcγRII/III antibody (manufactured by Pharmingen), anti-ClassI antibody (manufactured by Pharmingen), anti-mouse DX5 antibody (manufactured by e-Bio), or anti-ClassII antibody (manufactured by Pharmingen) were used. About 5 to 10 μg of the respective antibodies were reacted with an R cell ($1 \times 10^6$/100 μl) on ice for 30 minutes. The binding state of the antibodies was analyzed using FACS.

Figure 1:
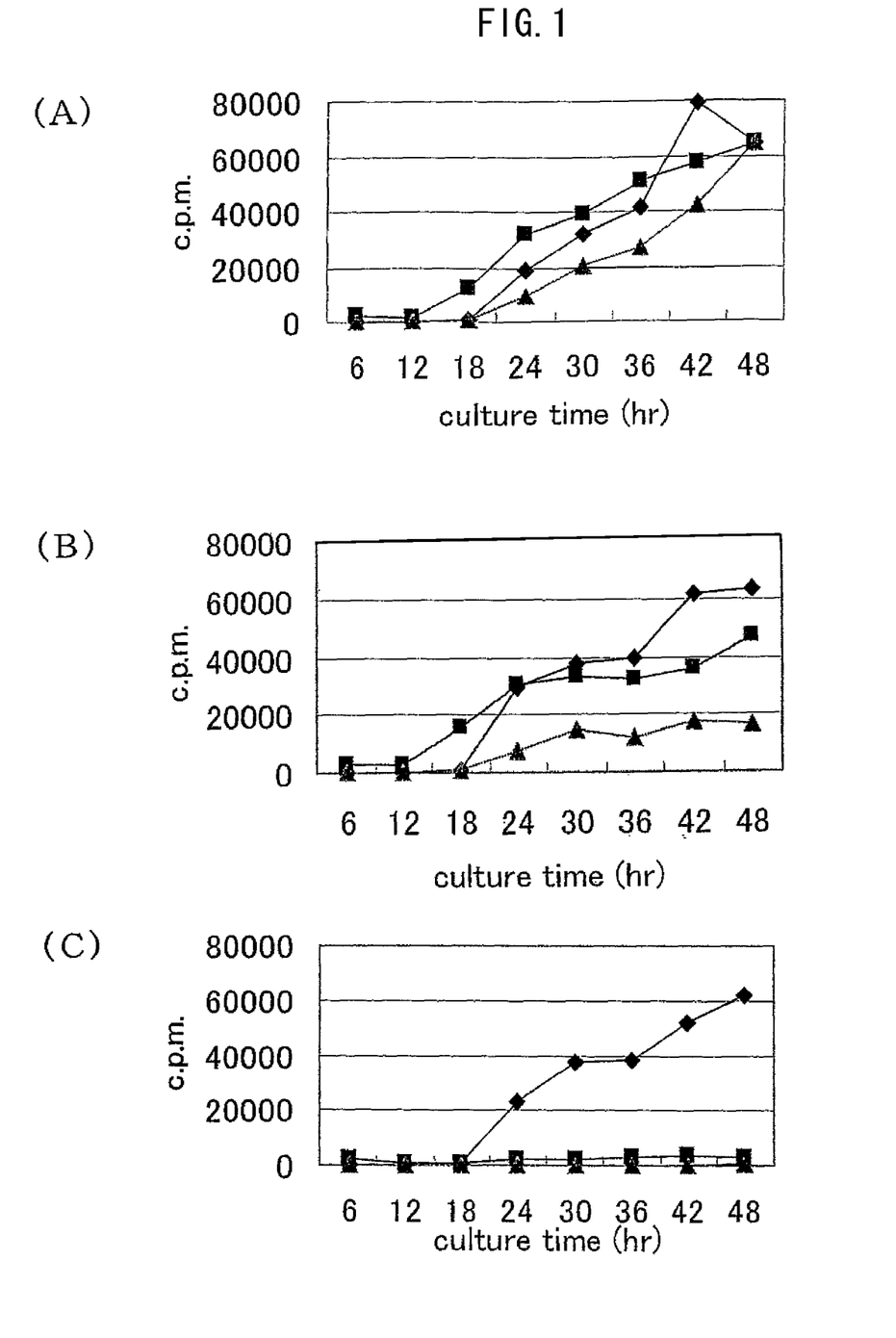

The results are shown in FIG. 1.

TABLE 1

|  | R cell | N62.5 cell | RCCM cell |
|---|---|---|---|
| FcεRIα | + | + | + |
| FcγRII/III | + | + | + |
| c-kit | + | + | + |
| ClassI | + | + | + |
| CD3 | − | − | − |
| B220 | − | − | − |
| DX5 | − | − | − |
| ClassII | − | − | − |

The morphology observation of various cell lines was performed using a light microscope and an electron microscope.

As a result, the cytoplasms of the R cells were stained pink with hematoxylin and eosin (HE staining). The cytoplasms were filled with many granules and some of them had a vacuole-like granular structure. On the other hand, unlike the mast cells, the R cells were not stained with Toluidine-blue (TB staining). In an electron microscope image, the cytoplasms had many cyst-like structures and the same granular structure as that of basophil was included therein. Additionally, the granular structure had a slightly large size, while a fingerprint-like and spiral-like structure were not found as observed in the mast cells. The cytoplasms were filled with many granules, while some of them were vacuolated (vacuole-like granular structure). These were different from mast cells having a high density granular structure.

These results showed that R cells were basophil-like or mast cell-like cell lines. N62.5 cells and RCCM cells had the same morphology.

Example 3

Experiments of Sensitivities of Various Cells to RCGF

R cells, N62.5 cells, or RCCM cells obtained in Example 1 were placed in each well of a 96-well microplate at a seeding density of $1.5 \times 10^4$ cells/well. A culture medium in which the content of RCGF was changed was used and the sensitivities of the cells to RCGF were confirmed.

The concentrations of RCGF were set to 10 v/v %, 0.1 v/v %, and 0 v/v %. The cells were cultured in an RPMI 1640 culture medium containing 10% by volume of serum at 37° C. in 5% $CO_2$ atmosphere for 48 hours. Thereafter, $^3$H-thymidine was added to the culture medium so as to give a final concentration of 0.5 μCi/ml, and the resultant was further cultured for 12 hours and the uptake amount of $^3$H during the time was measured. After the reaction, the uptake amount of $^3$H-thymidine was measured using MicroBeta TRIL UX (manufactured by WALLAC). The results are shown in FIG. 1. In FIGS. 1 (A) to (C), black rhombuses indicate RCCM cells, black squares indicate R cells, and black triangles indicate N62.5 cells.

As shown in FIG. 1, R cells (black square) and N62.5 cells (black triangle) proliferated depending on the concentration of RCGF (see FIGS. 1 (A) and (B)) and did not grow in the absence of RCGF (see FIG. 1 (C)). This showed that those cells were dependent on RCGF. The growth rate of N62.5 cells was reduced as the concentration of RCGF was lowered. This point showed that the reactivity of N62.5 cells was different from that of R cells (See, FIG. 1 (B)).

On the other hand, it was confirmed that RCCM cells (black rhombus) grew in the presence or absence of RCGF and that they were independent cells.

Therefore, despite the fact that the three cell lines were derived from the same spleen tissue, they had different reactivities to RCGF.

Example 4

Experiments of Cytokine Sensitivity of Various Cells

Figure 2:
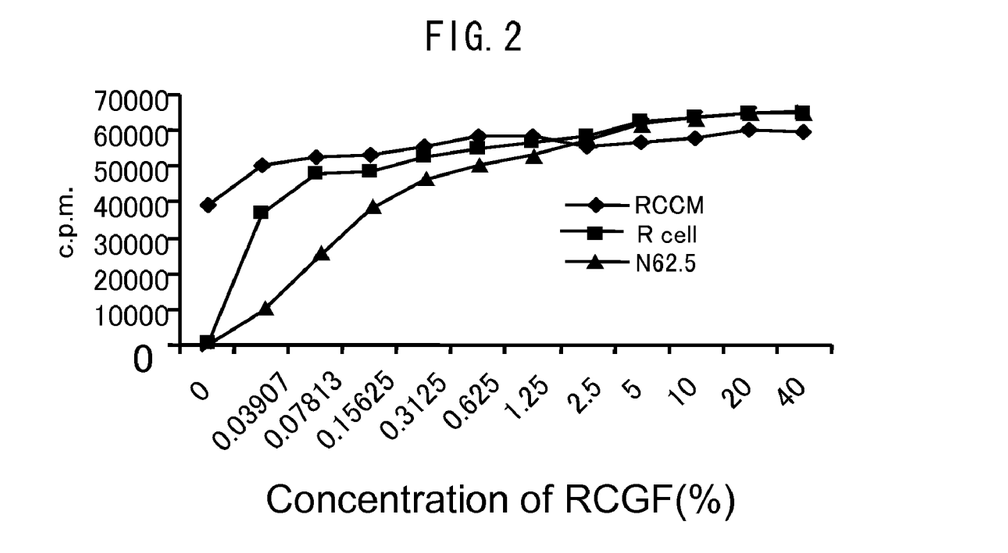
[FIG. 2] This is a graph showing the proliferative response of an R cell, an N62.5 cell, and an RCCM cell to various concentrations of RCGF containing a culture medium, according to the Examples of the present invention.
Figure 3:
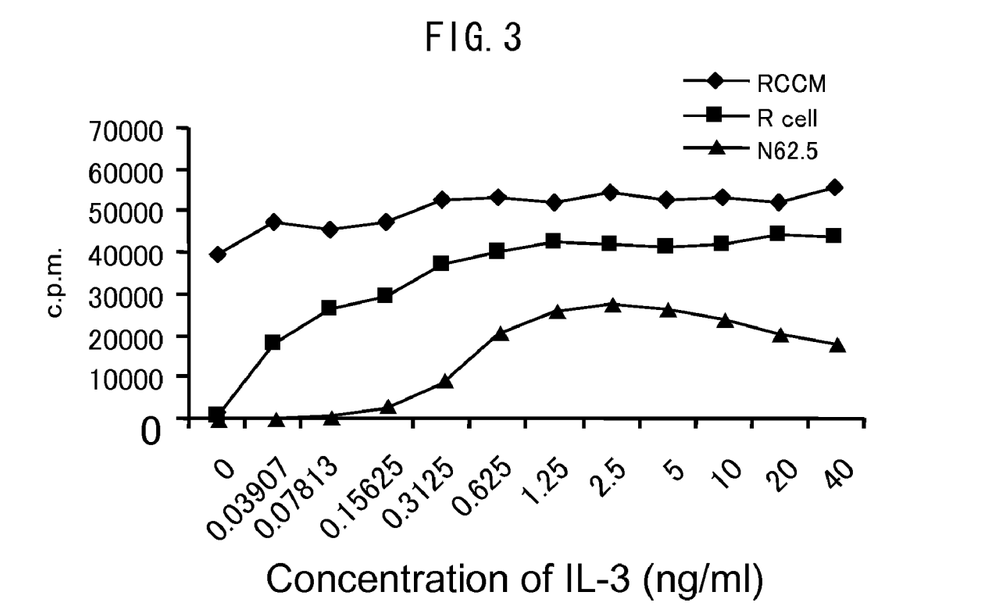
[FIG. 3] This is a graph showing the proliferative response of an R cell, an N62.5 cell, and an RCCM cell to various concentrations of IL-3 containing a culture medium, according to the Examples of the present invention.
Figure 4:
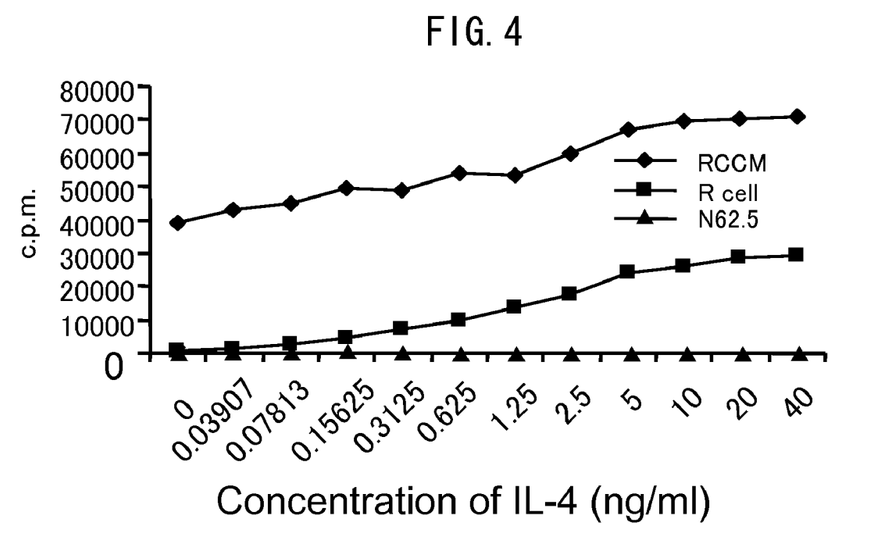
[FIG. 4] This is a graph showing the proliferative response of an R cell, an N62.5 cell, and an RCCM cell to various concentrations of IL-4 containing a culture medium, according to the Examples of the present invention.
Figure 5:
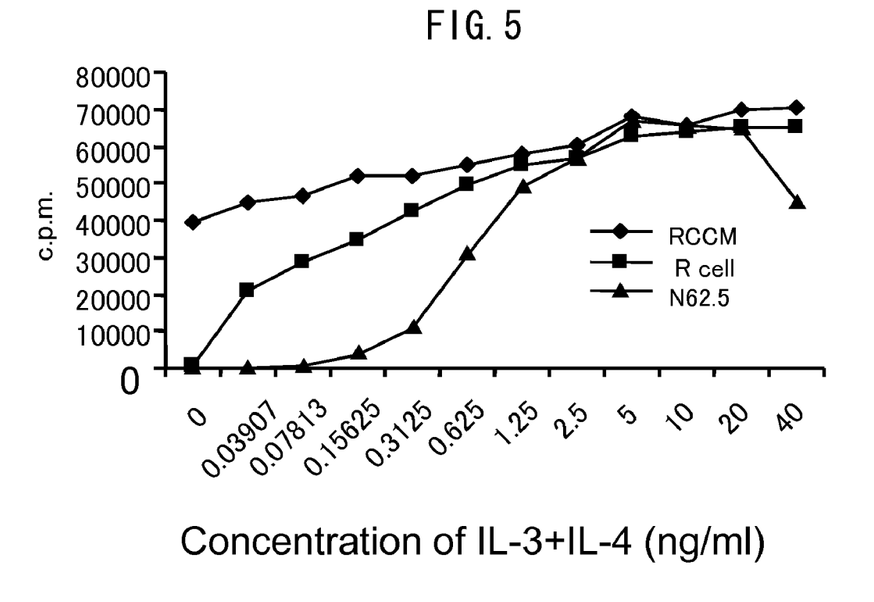
[FIG. 5] This is a graph showing the proliferative response of an R cell, an N62.5 cell, and an RCCM cell to various concentrations of IL-3+IL-4 containing a culture medium, according to the Examples of the present invention.

R cells, N62.5 cells, or RCCM cells obtained in Example 1 were placed in each well of a 96-well microplate at a seeding density of $1.5 \times 10^4$ cells/well. Then, the sensitivities of the cells to RCGF (FIG. 2) and various cytokines (FIG. 3: IL-3, FIG. 4: IL-4, FIG. 5: IL-3+IL-4) were confirmed.

Culture media containing various recombinant cytokines (IL-3 [manufactured by PeproTech]) and IL-4 [manufactured by PeproTech] were added to each well, and cultured at 37° C. in 5% $CO_2$ atmosphere for 48 hours. In this regard, the concentration of RCGF was based on ½ serial dilutions (starting with 80% by volume of the culture medium). The amount of cytokine was based on ½ serial dilutions (starting with 40 ng/ml). The amount of combination of IL-3 and IL-4 was based on ½ serial dilutions (starting with 20 ng/ml). Thereafter, $^3$H-thymidine was added to the culture medium so as to give a final concentration of 0.5 μCi/ml, and the resultant was further cultured for 12 hours and the uptake amount of $^3$H during the time was measured. The results are shown in FIGS. 2 to 5. In FIGS. 2 to 5, black rhombuses indicate RCCM cells, black squares indicate R cells, and black triangles indicate N62.5 cells.

As shown in FIGS. 2 to 5, the sensitivities of the three cell lines according to the Examples with respect to IL-3 (refer to FIG. 3), IL-4 (See, FIG. 4), and IL-3+IL-4 (See, FIG. 5) were respectively different, similarly to the respective sensitivities to RCGF. Particularly, N62.5 cells did not show sensitivity to IL-4, but showed proliferative activity to IL-3. The difference in reactivity between N62.5 cells and R cells was clear. On the other hand, there was no difference in growth potential of RCCM cells in each case, suggesting that RCCM cells were always in a proliferative state.

As described above, the three cell lines according to the Examples showed different properties to not only RCGF but also to allergic cytokines such as IL-3 or IL-4. Therefore, it was clear that the three cell lines could be used to screen for intracellular molecules corresponding to differences in reactivities to various cytokines between the cell lines or substances involved in the gene expression.

Example 5

Figure 6:
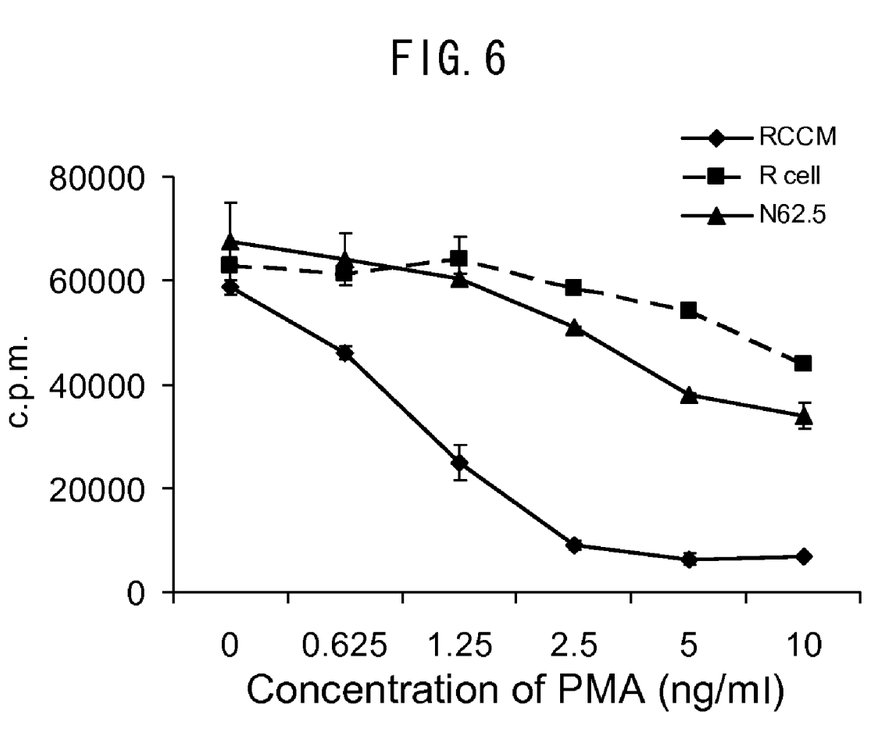
[FIG. 6] This is a graph showing the proliferative response of various cell lines to PMA, according to the Examples of the present invention.

R cells, N62.5 cells, or RCCM cells obtained in Example 1 were placed in each well of a 96-well microplate at a seeding density of 1.5×10⁴ cells/well in the same manner as described in Example 4. ½ serial dilutions (starting with 10 ng/ml) of phorbol 12-myristate 13 acetate (PMA) were added to each well, and culturing was performed at 37° C. in 5% $CO_2$ atmosphere for 48 hours. Thereafter, ³H-thymidine was added to the culture medium so as to give a final concentration of 0.5 µCi/ml, which was further cultured for 12 hours and the uptake amount of ³H during the time was measured. The results are shown in FIG. 6. In FIG. 6, black rhombuses indicate RCCM cells, black squares indicate R cells, and black triangles indicate N62.5 cells.

As shown in FIG. 6, RCCM cells were different from N62.5 cells and R cells and the proliferation of RCCM cells was suppressed by a low concentration of PMA. This suggests that PMA has a function as a chronic allergic disease-related substance.

Thus, when the three cell lines (RCCM cells, N62.5 cells, and R cells) were used, there were differences in reactivity to growth potentials of these cell lines. Therefore, they can be applied to screening of growth-inhibiting substances as an allergic disease-related substance such as PMA.

Example 6

Figure 7:
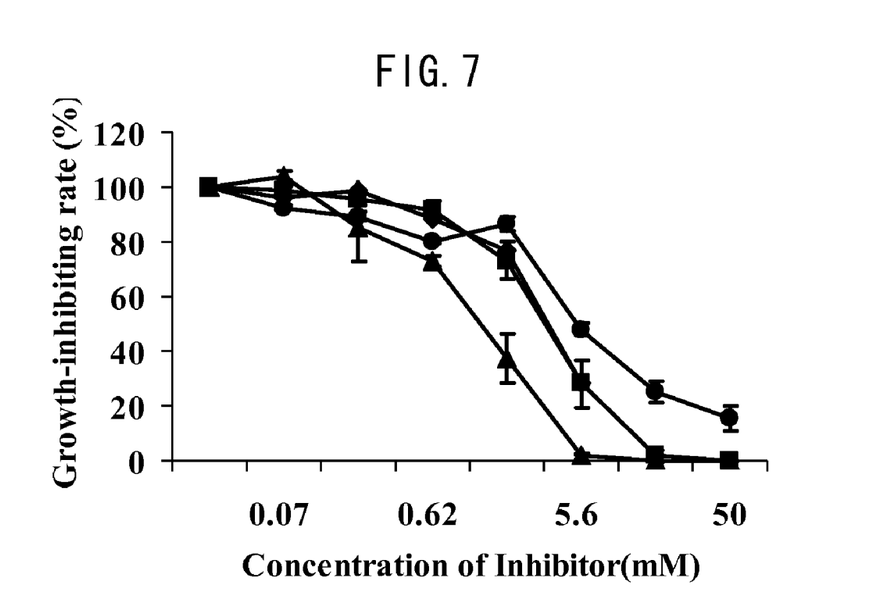
[FIG. 7] This is a graph showing the proliferative response of various cell lines to LY294002, according to the Examples of the present invention.
Figure 8:
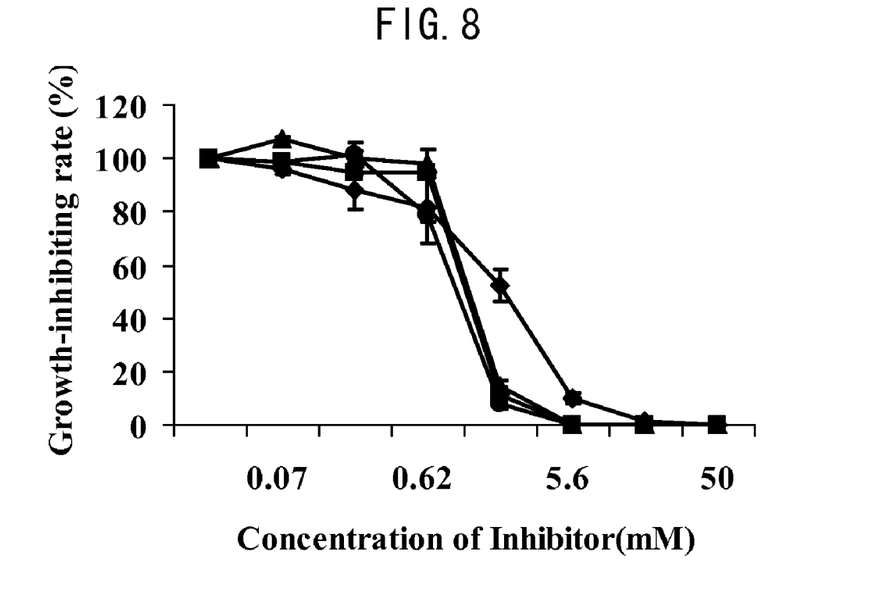
[FIG. 8] This is a graph showing the proliferative response of various cell lines to Rottlerin, according to the Examples of the present invention.

R cells, N62.5 cells, or RCCM cells obtained in Example 1 and P185 cells (a basophil-like cell line) were placed in each well of a 96-well microplate at a seeding density of 1.5×10⁴ cells/well in the same manner as described in Example 4. ½ serial dilutions (starting with 10 ng/ml) of LY294002 (a PI3K inhibitor; Cat No. FA-002, manufactured by SuperArray) and Rottlerin (a PKC inhibitor; Cat No. 557370, manufactured by CALBIOCHEM) were added to each well, which was cultured at 37° C. in a 5% $CO_2$ atmosphere for 48 hours. Thereafter, ³H-thymidine was added to the culture medium so as to give a final concentration of 0.5 µCi/ml, and culturing was further performed for 12 hours and the uptake amount of ³H during the time was measured. The results are shown in FIG. 7. In FIGS. 7 and 8, black squares indicate R cells, black triangles indicate N62.5 cells, black rhombuses indicate RCCM cells, and black circles indicate P185. FIG. 7 is a graph showing the response of respective cells to LY294002. FIG. 8 is a graph showing the response of respective cells to Rottlerin.

As shown in FIG. 7, the proliferation of RCCM cells was suppressed by a lower concentration of LY294002 (the PI3K inhibitor) as compared to the cases of the other two cell lines. The reactivity of R cells was almost the same reactivity as that of N62.5 cells. This suggests that LY294002 is a chronic allergic disease-related substance.

On the other hand, as shown in FIG. 8, when Rottlerin (the PKC inhibitor) was used, the proliferation of three cell lines according to the invention was rapidly suppressed as compared to the growth inhibition of the basophil-like cell line P815. However, the RCCM cells, N62.5 cells, and R cells each showed the same reactivity.

Thus, even if the inhibitors were used as growth-related substances, there were differences in reactivity to allergic disease. The allergic disease-related substances can be further classified by using the combination of the cell lines according to the invention.

According to the invention, when the three cell lines (RCCM cells, N62.5 cells, and R cells) were used, there were differences in reactivity to the growth potentials of these cell lines. Therefore, they can be applied to screening of growth-inhibiting substances as an allergic disease-related substance such as PMA.

In the Examples, the allergic disease-related substance was screened in accordance with the growth rate based on the amount of uptake of ³H-thymidine. However, the invention is not limited thereto.

For example, the pattern of the gene expression of various cells before and after contacting with the candidate substance is observed by the subtraction method or the like. At this time, some or all of the genes of the respective cells are immobilized on the microarray and the gene expression pattern after the contact is observed using a fluorescence detecting agent. As a result, the candidate substances can be screened based on the presence or absence of gene expression.

As described in the Examples, since R cells, N62.5 cells, and RCCM cells according to the invention have different reactivities to the allergic cytokines, they can be used as an effective panel in order to screen for an allergic disease-related substance.

Therefore, according to the present invention, the screening for an allergic disease-related substance can be efficiently performed.

---

---

The invention claimed is:

1. A method for screening an allergic disease-related molecule, the method comprising:

providing a candidate substance, providing at least two basophil-like or mast cell-like cell lines selected from the group consisting of an R cell (Accession No. FERM BP-10918), an N62.5 cell (Accession No. FERM BP-10919), and an RCCM cell (Accession No. FERM BP-10920),
contacting said cells with the candidate substance, and
determining whether the candidate substance is an allergic disease-related molecule based on reactivity of said cells to the candidate substance.

2. A method for screening an allergic disease-related molecule, the method comprising:
providing a candidate substance,
providing at least one basophil-like or mast cell-like cell line selected from the group consisting of an R cell (Accession No. FERM BP-10918), an N62.5 cell (Accession No. FERM BP-10919), and an RCCM cell (Accession No. FERM BP-10920),
contacting said cell with the candidate substance, and
determining whether the candidate substance is an allergic disease-related molecule based on reactivity of said cell to the candidate substance.

3. The screening method according to claim 1, wherein the screening screens candidate substances with different effects on a plurality of cell lines used for the screening.

4. The screening method according to claim 1, wherein the screening method is carried out in the presence of a competitive compound.

5. The screening method according to claim 1, wherein the candidate substance is a candidate substance for a compound having a function to control cytokine sensitivity.

6. The screening method according to claim 1, wherein the screening is carried out based on any one of changes in cell morphology and cell activity, biochemical changes in molecules involved in intracellular signaling transduction, or changes in genetic regulation of cells.

7. The screening method according to claim 2, wherein the screening method is carried out in the presence of a competitive compound.

8. The screening method according to claim 2, wherein the candidate substance is a candidate substance for a compound having a function to control cytokine sensitivity.

9. The screening method according to claim 2, wherein the screening is carried out based on any one of changes in cell morphology and cell activity, biochemical changes in molecules involved in intracellular signaling transduction, or changes in genetic regulation of cells.

10. A basophil-like or mast cell-like cell line, wherein the cell line is an R cell (Accession No. FERM BP-10918), an N62.5 cell (Accession No. FERM BP-10919), or an RCCM cell (Accession No. FERM BP-10920).

11. A cell set comprising at least two selected from the group consisting of an R cell (Accession No. FERM BP-10918), an N62.5 cell (Accession No. FERM BP-10919), and an RCCM cell (Accession No. FERM BP-10920) and is used for screening for an allergic disease-related compound.

* * * * *

SEQUENCE LISTING

<160> NUMBER OF SEQ ID NOS: 1

<210> SEQ ID NO 1
<211> LENGTH: 17
<212> TYPE: PRT
<213> ORGANISM: Artificial
<220> FEATURE:
<223> OTHER INFORMATION: OVA323-339

<400> SEQUENCE: 1

Ile Ser Gln Ala Val His Ala Ala His Ala Glu Ile Asn Glu Ala Gly
1               5                   10                  15

Arg